US006472514B2

(12) United States Patent
Kuroda

(10) Patent No.: US 6,472,514 B2
(45) Date of Patent: Oct. 29, 2002

(54) ELECTRON TRANSPORT COMPOUNDS

(75) Inventor: Masami Kuroda, Kanagawa (JP)

(73) Assignee: Fuji Electric Imaging Device Co., Ltd., Nagano (JP)

( * ) Notice: Subject to any disclaimer, the term of this patent is extended or adjusted under 35 U.S.C. 154(b) by 0 days.

(21) Appl. No.: 09/883,855

(22) Filed: Jun. 18, 2001

(65) Prior Publication Data

US 2002/0052519 A1 May 2, 2002

Related U.S. Application Data

(63) Continuation-in-part of application No. 09/428,842, filed on Oct. 28, 1999, now Pat. No. 6,268,095.

(30) Foreign Application Priority Data

Oct. 29, 1998 (JP) .......................................... 10-308279

(51) Int. Cl.[7] .............................................. C07C 245/06
(52) U.S. Cl. ....................................... 534/816; 534/885
(58) Field of Search ................................. 534/816, 885

(56) References Cited

PUBLICATIONS

Rieker et al., Chemical Abstracts, 69:51403, 1968.*

* cited by examiner

*Primary Examiner*—Flona T. Powers
(74) *Attorney, Agent, or Firm*—Darby & Darby

(57) ABSTRACT

The present invention provides a new charge transport agent for use in a photosensitive layer in a positive-electrification-type electrophotographic photoconductor that can be used with high speed copying machines. The electrophotographic photoconductor of the invention includes an electrically conductive substrate and a photosensitive layer on the substrate. The photosensitive layer contains a charge generation agent and an electron transport compound described by the following general formula (I).

(I)

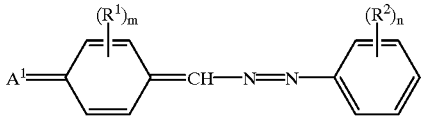

wherein $R^1$ and $R^2$ are each independently a halogen atom, a substituted or unsubstituted alkyl group having from 1 to 8 carbon atoms, a substituted or unsubstituted alkoxy group having form 1 to 8 carbon atoms, an arylalkyl group, a substituted or unsubstituted aryl group or a residue for forming a ring. $A^1$ is an oxygen atom, m is an integer from 0 to 4 and n is an integer from 0 to 5.

27 Claims, 20 Drawing Sheets

(I)

(II)

(I-1)

(I-2)

(I-3)

(I-4)

(I-5)

(I-6)

(I-7)

(I-8)

(I-9)

(I-10)

(I-11)

(I-13)

(I-17)

(I-18)

(II-1)

(II-2)

(II-3)

(II-4)

(II-5)

(III)

(IV)

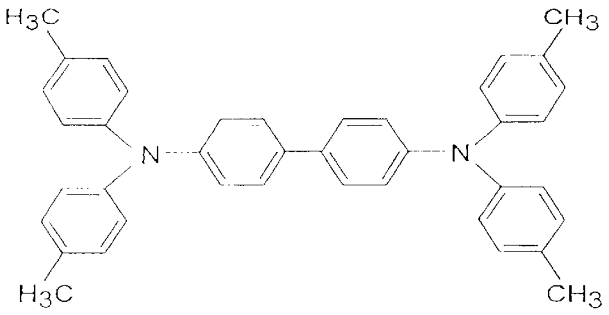
FIG. 11
FIG. 12
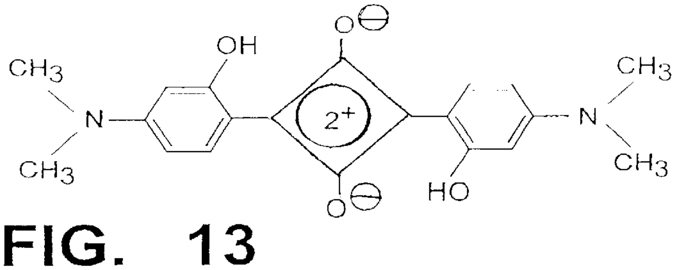
FIG. 13
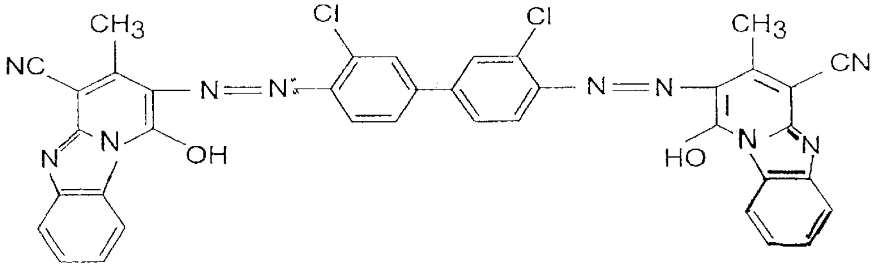
FIG. 14
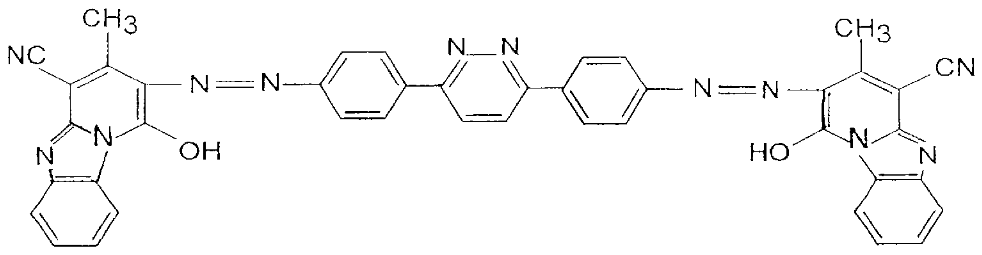

(III)

(III) (I-1)

(III-1)

(III-1) (I-17)

(III-2)

(III-2)

(I-11)

(III-3)

(III-3)

(I-18)

(III-4)

(III-4)

(I-3)

( IV-1 )

( IV-1 )

( II-1 )

ELECTRON TRANSPORT COMPOUNDS

This is a continuation-in-part of application Ser. No. 09/428,842, filed Oct. 28, 1999 now U.S. Pat. No. 6,268,095, issued on Jul. 31, 2001.

BACKGROUND OF THE INVENTION

The present invention relates to new electron transport compounds and a photoconductor for electrophotography (hereinafter referred to as an "electrophotographic photoconductor" or simply as a "photoconductor"). Specifically, the present invention relates to an electrophotographic photoconductor that includes a photosensitive layer of organic materials on an electrically conductive substrate which is used in printers and copying machines that employ electrophotographic techniques.

Conventional photoconductors for printers, facsimiles and copying machines using electrophotographic techniques include an inorganic photoconductive material such as selenium or alloys of selenium. Other inorganic photoconductive materials such as zinc oxide and cadmium sulfide dispersed in a resin binder have also been used. Recently, research and development has been performed to investigate the use of organic photoconductive materials in electrophotographic photoconductors. Some organic electrophotographic photoconductors exhibiting improved sensitivity and durability have been developed.

Photoconductors must retain surface charges in the dark, generate charges in response to received light and transport charges in response to the received light. The so-called single-layer-type photoconductor includes a layer that exhibits all the aforementioned functions. The so-called laminate-type photoconductor includes a laminate consisting of a layer that contributes to charge generation and a layer that contributes to surface charge retention in the dark and charge transport under light exposure.

Electrophotography using the aforementioned photoconductors can form images using, for example, the Carlson process. The Carlson process includes the steps of electrifying the photoconductor by corona discharge in the dark, forming electrostatic latent images of original letters and pictures by light irradiation onto the electrified photoconductor, developing the latent images with toner, and fixing (copying) the developed toner images on a carrier such as paper. After the toner images are copied, the charges on the photoconductor are removed, the residual toner is removed, the optical charge is removed and the photoconductor is prepared for the next image formation.

The organic photoconductors developed so far are superior to the inorganic photoconductors in flexibility, ease of film formation, low manufacturing costs and safety. Further improvements of the sensitivity and durability of the organic photoconductors have been studied using a variety of organic materials.

Most of the organic photoconductors are of a laminate-type which distributes the foregoing basic functions among a charge generation layer and a charge transport layer. Usually, the laminate-type photoconductor includes an electrically conductive substrate; a charge generation layer on the substrate, containing a charge generation agent such as pigment or dye; and a charge transport layer, containing a charge transport agent such as hydrazone and triphenylamine on the charge generation layer. Due to the electron donating nature of the charge transport agent, the laminate-type photoconductor is usually a hole-transport-type, which exhibits sensitivity when its surface is negatively electrified.

The corona discharge for negative electrification is more unstable than that for positive electrification and generates ozone and nitrogen oxide. The ozone and nitrogen oxide that are generated, absorb to the photoconductor surface, resulting in deterioration of the photoconductor physically and chemically. The ozone and nitrogen oxide are also hazardous to the environment. The photoconductor of a positive-electrification-type is superior to the negative-electrification-type of photoconductor, since the positive-electrification-type photoconductor can be used in a greater variety of working conditions. The fields to which the positive-electrification-type photoconductor is applicable are wider.

Due to the limitations of the negative-electrification-type photoconductors, research has been done to develop photoconductors for positive electrification. For example, single-layer-type photoconductors has been proposed which includes a photosensitive layer where a charge generation agent and a charge transport agent are dispersed in a resin binder. Some of these are used practically. However, the single-layer-type photoconductor is not sensitive enough to be applicable to high-speed machines. In addition, the single-layer-type photoconductor must have sufficient stability during repeated use.

To improve sensitivity, a positive-electrification-type photoconductor has been proposed which has a function-separation-type laminate with a charge generation layer laminated on a charge transport layer. However, corona discharge, light irradiation and mechanical wear interfere with stability under repeated use, since this type of photoconductor has a charge generation layer in its surface. Placing a protection layer on the charge generation layer has been proposed to obviate the aforementioned problems. Although the protection layer improves mechanical wear resistance, it interferes with the ability to improve the electrical properties of the photoconductor, including sensitivity.

A positive-electrification-type photoconductor that includes a function-separation-type laminate of a charge transport layer containing an electron transport agent, on a charge generation layer, has also been proposed. The electron transport agent such as 2,4,7-trinitro-9-fluorenone is known to those skilled in the art. However, this electron transport agent is carcinogenic and hazardous to human health. Although other electron transport agents such as cyanine compounds and quinone compounds have been proposed (cf. Japanese Unexamined Laid Open Patent Applications No. S50-131941, No. H06-59483, No. H06-123986 and No. H09-190003), a compound exhibiting sufficient electron transport capability has not yet been obtained.

OBJECTS AND SUMMARY OF THE INVENTION

In view of the foregoing, it is an object of the invention to provide a new charge transport agent and a positive-electrification-type electrophotographic photoconductor that obviates the foregoing problems. It is another object of the invention to provide a positive-electrification-type electrophotographic photoconductor that contains the charge transport agent in its photosensitive layer and can be used in high-speed copying machines and printers.

The inventor of the present invention has examined various organic materials to achieve the foregoing objects. As a result of many experiments, the present inventor has found that a specific compound described by the general formula (I) in FIG. 3 or (II) in FIG. 4 is very effective in improving electrophotographic properties and in obtaining high sensitivity in positive-electrification-type photoconductors. The precise mechanism has not yet been well defined.

As used herein, the term "alkyl" is defined to include substituted or unsubstituted straight or branched carbon chains. An "aryl" group is defined as a substituted or unsubstituted carbocyclic or heterocyclic aromatic ring system. A substituent for a substituted alkyl, alkoxy or aryl group is defined to include one or more chemically feasible substituents that would be well known to one skilled in the art. Such substituents may include at least one of the following: a straight, branched or cyclic alkyl or alkenyl group, an alkoxy group, an alkoxycarbonyl group or a halogen atom.

Advantageously, $R^1$'s are different from each other when m is 2 or more.

Advantageously, $R^2$'s are identical to each other for n of 2 or more.

Advantageously, $R^2$'s are different from each other for n of 2 or more.

According to another aspect of the invention, a new charge transport compound in a photosensitive layer of a positive-electrification-type electrophotographic photoconductor is provided that can be used with high speed copying machines. The new charge transport agent is described by the following general formula (II):

(II)

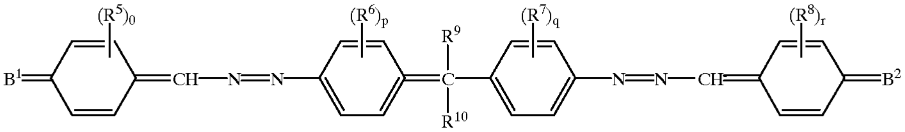

Briefly stated, the present invention provides a new charge transport agent in a photosensitive layer of a positive-electrification-type electrophotographic photoconductor that can be used with high speed copying machines. The charge transport agent is described by the following general formula (I):

(I)

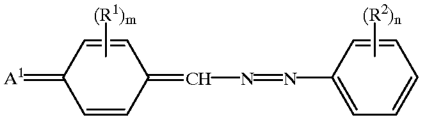

wherein $R^1$ and $R^2$ are each independently a halogen atom, a substituted or unsubstituted alkyl group having from 1 to 8 carbon atoms, a substituted or unsubstituted alkoxy group having from 1 to 8 carbon atoms, an arylalkyl group, a substituted or unsubstituted aryl group or a residue for forming a ring. $A^1$ is an oxygen atom, m is an integer from 0 to 4 and n is an integer from 0 to 5.

According to an aspect of the invention, a photoconductor for electrophotography is provided including: an electrically conductive substrate and a photosensitive layer on the electrically conductive substrate. The photosensitive layer contains a charge generation agent and a charge transport agent. The charge transport agent includes an electron transport compound described by the general formula (I) in FIG. 3; where $R^1$ and $R^2$ are each independently a halogen atom, a substituted or unsubstituted alkyl group having from 1 to 8 carbon atoms, a substituted or unsubstituted alkoxy group having from 1 to 8 carbon atoms, an arylalkyl group, a substituted or unsubstituted aryl group, or a residue forming a ring. $A^1$ is an oxygen atom; m is 0, 1, 2, 3 or 4; and n is 0, 1, 2, 3, 4 or 5.

Advantageously, the $R^1$ and $R^2$ substituents are alkyl groups.

Advantageously, the $R^1$ and $R^2$ substituents are alkoxy groups.

Advantageously, the $R^1$ and $R^2$ substituents are aryl groups.

Advantageously, $R^1$'s are identical to each other when m is 2 or more.

wherein $R^5$, $R^6$, $R^7$ and $R^8$ are each independently selected from the group consisting of a halogen atom and an alkyl group having from 1 to 8 carbon atoms; $R^9$ and $R^{10}$ are each independently selected from the group consisting of a hydrogen atom, an alkyl group having from 1 to 8 carbon atoms and an aryl group; $B^1$ and $B^2$ are an oxygen atom; and o, p, q and r are each independently an integer from 0 to 4.

According to a further aspect of the invention, a photoconductor for electrophotography is provided including an electrically conductive substrate and a photosensitive layer on the electrically conductive substrate. The photosensitive layer contains a charge generation agent and a charge transport agent. The charge transport agent includes an electron transport compound described by the general formula (II) in FIG. 4; where $R^5$ is a halogen atom, or an alkyl group having from 1 to 8 carbon atoms; $R^6$ is a halogen atom, or an alkyl group having from 1 to 8 carbon atoms; $R^7$ is a halogen atom, or an alkyl group having from 1 to 8 carbon atoms; $R^8$ is a halogen atom, or an alkyl group having from 1 to 8 carbon atoms; $R^9$ is a hydrogen atom, an alkyl group having from 1 to 8 carbon atoms, or an aryl group; $R^{10}$ is a hydrogen atom, an alkyl group having from 1 to 8 carbon atoms, or an aryl group; $B^1$ is an oxygen atom; $B^2$ is an oxygen atom; o is 0, 1, 2, 3 or 4; p is 0, 1, 2, 3 or 4; q is 0, 1, 2, 3 or 4; r is 0, 1, 2, 3 or 4; $R^5$'s are identical to or different from each other for o of 2 or more; $R^6$'s are identical to or different from each other for p of 2 or more; $R^7$'s are identical to or different from each other for q of 2 or more; and $R^8$'s are identical to or different from each other for r of 2 or more.

Advantageously, the $R^5$, $R^6$, $R^7$ and $R^8$ substituents are alkyl groups.

Advantageously, the $R^9$ and $R^{10}$ substituents are aryl groups.

Advantageously, $R^5$'s are identical each other for o of 2 or more.

Advantageously, $R^5$'s are different from each other for o of 2 or more.

Advantageously, $R^6$'s are identical to each other for p of 2 or more.

Advantageously, $R^6$'s are different from each other for p of 2 or more.

Advantageously, $R^7$'s are identical each other for q of 2 or more.

Advantageously, $R^7$'s are different from each other for q of 2 or more.

Advantageously, $R^8$'s are identical to each other for r of 2 or more.

Advantageously, $R^8$'s are different from each other for r of 2 or more.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 11 describes the structural formula of another benzidine derivative used in the photosensitive layer according to the present invention.

FIG. 12 describes the structural formula of a squalane compound used in substitution for titanyl phthalocyanine according to the present invention.

FIG. 13 describes the structural formula of a bisazo pigment used in substitution for titanyl phthalocyanine according to the present invention.

FIG. 14 describes the structural formula of another bisazo pigment used in substitution for titanyl phthalocyanine according to the present invention.

DETAILED DESCRIPTION OF THE PREFERRED EMBODIMENTS

Figure 7A:
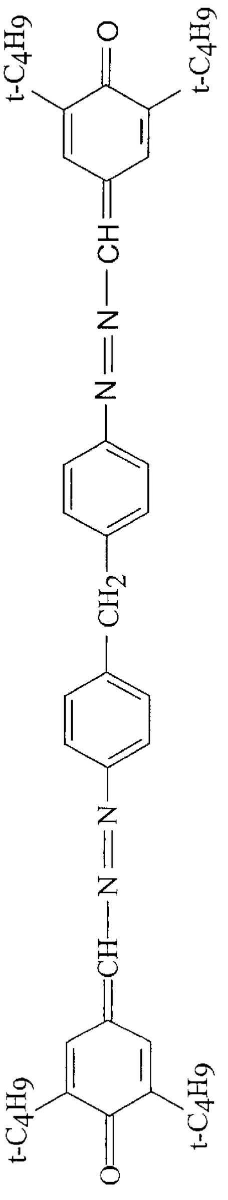
FIGS. 7A and 7B describe the structural formulae (II-1) through (II-5) of the electron transport compounds described by the general formula (II) according to the present invention.
Figure 7A:
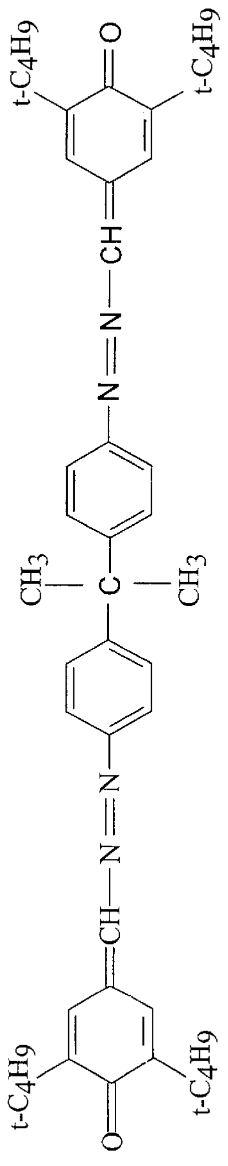
Figure 7A:
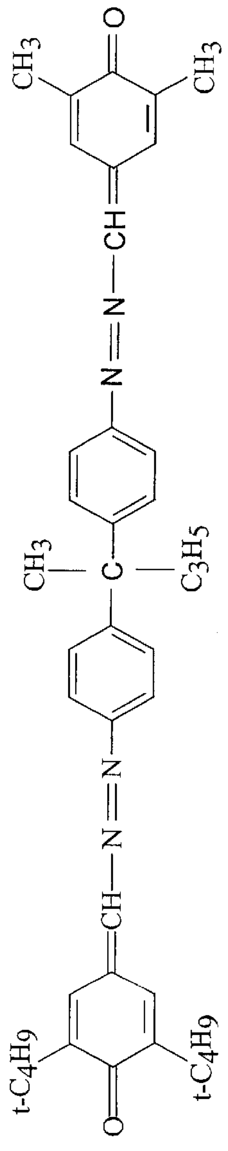
Figure 7B:
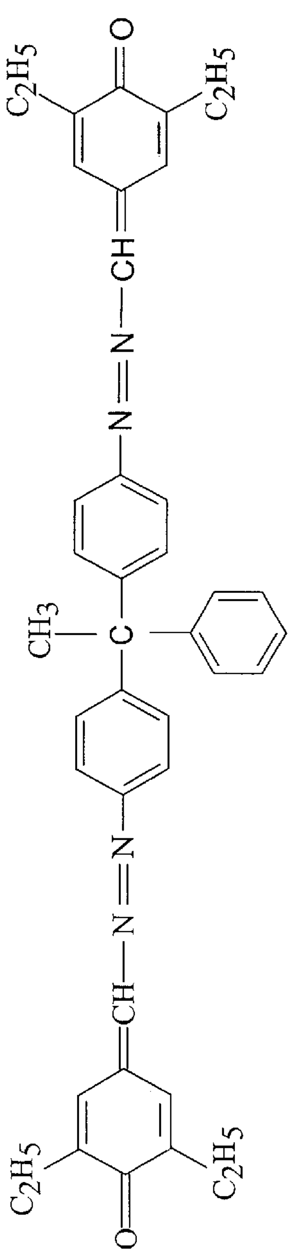
Figure 7B:
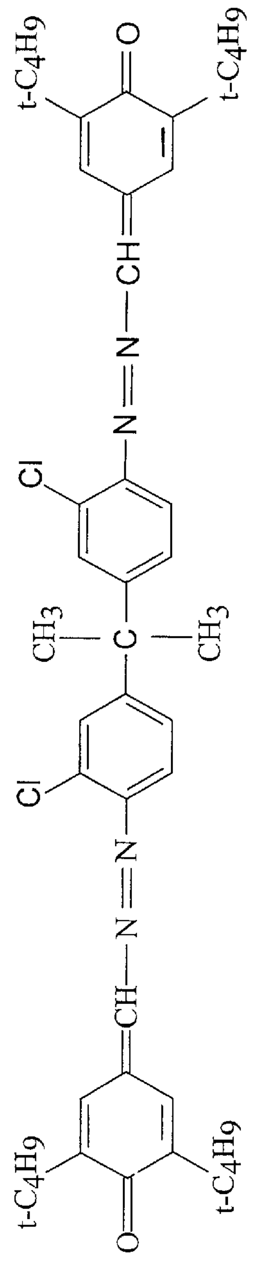

The structural formulae (I-1) through (I-18) show examples of the compounds described by general formula (I) and are described in FIGS. 5A and 5B and FIGS. 6A and 6B. The structural formulae (II-1) through (II-8) show some examples of the compounds described by general formula (II) and are described in FIGS. 7A and 7B.

Figure 8:
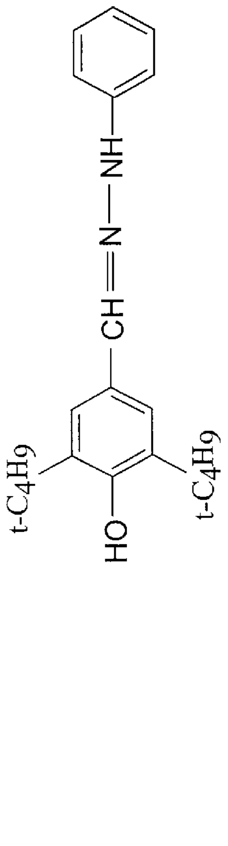
FIG. 8 describes the structural formula (III) of the starting material for synthesizing the electron transport compound (I-1).
Figure 9:
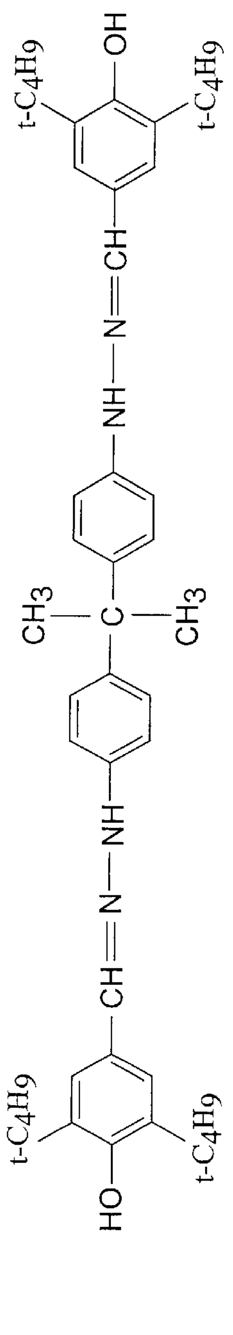
FIG. 9 describes the structural formula (IV) of the starting material for synthesizing the electron transport compound (II-2).

The compounds described by the general formula (I) or (II) are synthesized by conventional methods. For example, the compound described by structural formula (I-1) is synthesized by oxidizing the compound described by the structural formula (III) in FIG. 8 in an organic solvent (i.e. chloroform) using an appropriate oxidizing agent (i.e. potassium permanganate). The compound described by the structural formula (II-2) is synthesized by oxidizing the compound described by the structural formula (IV) in FIG. 9 in an organic solvent (i.e. chloroform) using an appropriate oxidizing agent (i.e. potassium permanganate).

Figure 1:
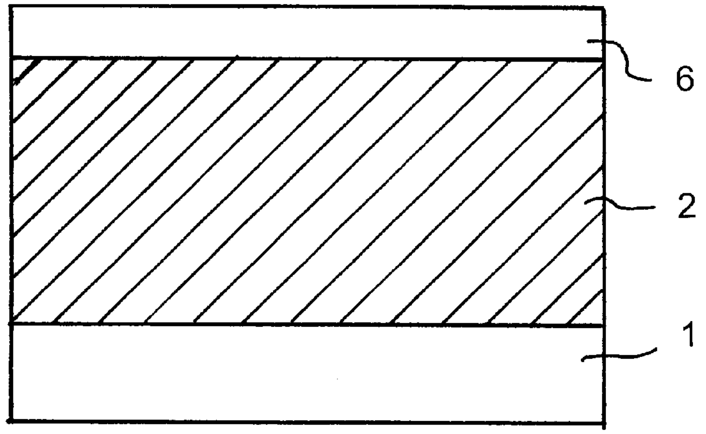
FIG. 1 is a cross section of a single-layer-type electrophotographic photoconductor.
Figure 2:
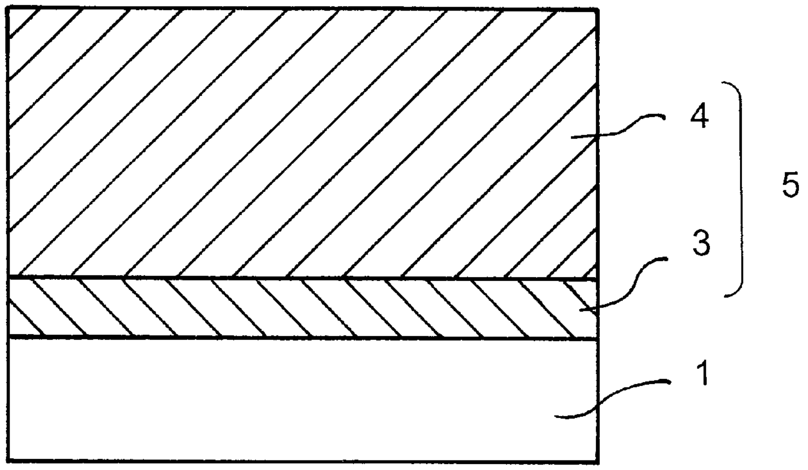
FIG. 2 is a cross section of a laminate-type electrophotographic photoconductor.
Figure 3:
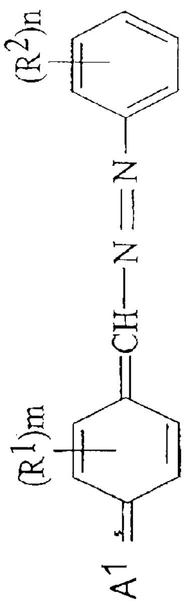
FIG. 3 describes the general formula (I) of the electron transport compounds according to the present invention.
Figure 4:
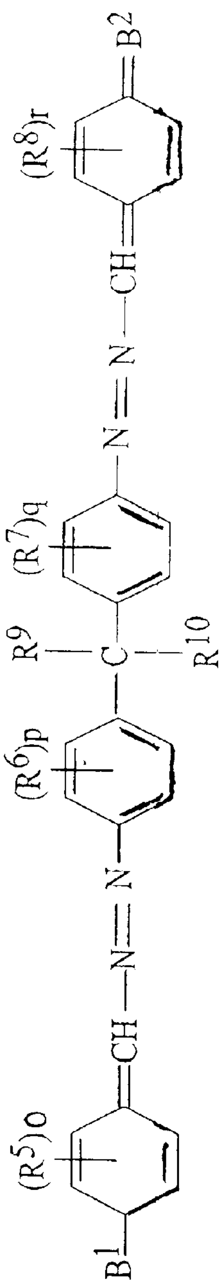
FIG. 4 describes the general formula (II) of additional electron transport compounds according to the present invention.
Figure 5A:
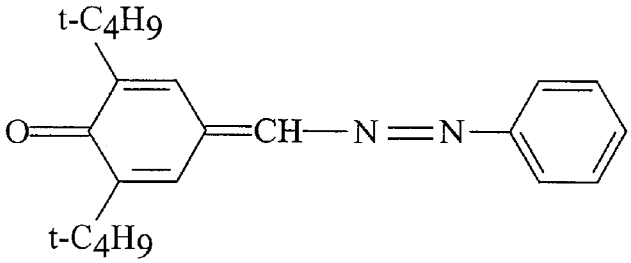
FIGS. 5A and 5B describe the structural formulae (I-1) through (I-8) of the electron transport compounds described by the general formula (I) according to the present invention.
Figure 5A:
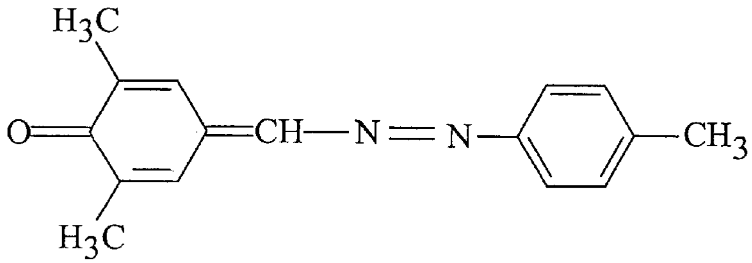
Figure 5A:
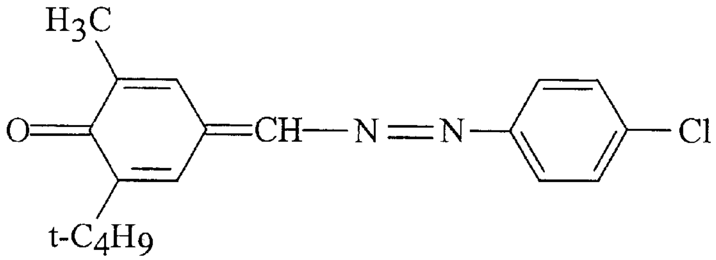
Figure 5A:
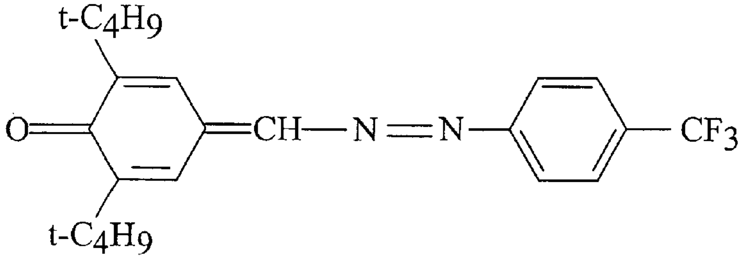
Figure 5B:
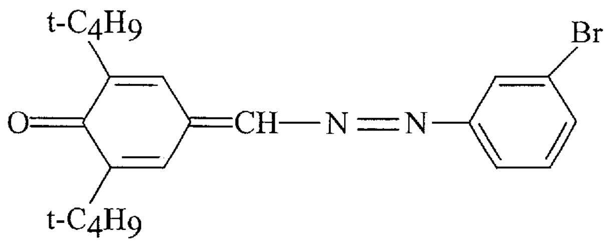
Figure 5B:
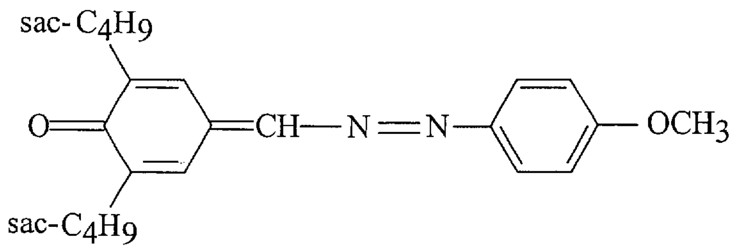
Figure 5B:
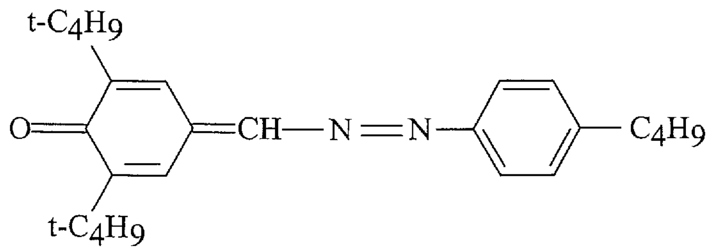
Figure 5B:
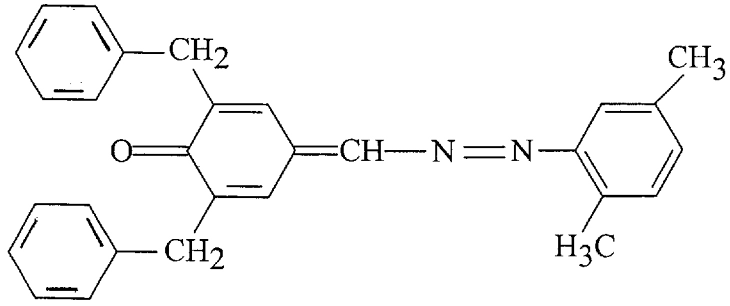
Figure 6A:
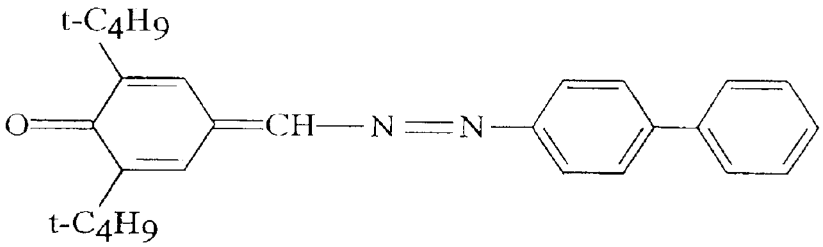
FIGS. 6A and 6B describe the structural formulae (I-9) through (I-18) of the electron transport compounds described by the general formula (I) according to the present invention.
Figure 6A:
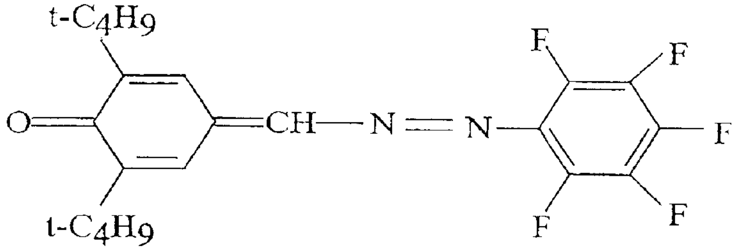
Figure 6A:
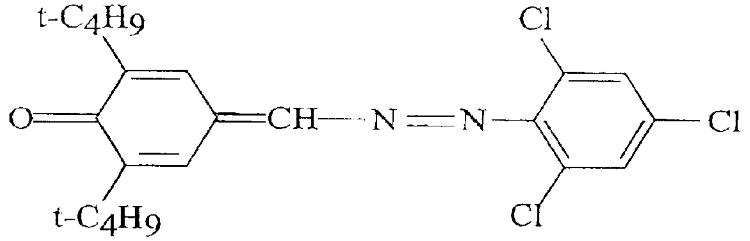
Figure 6A:
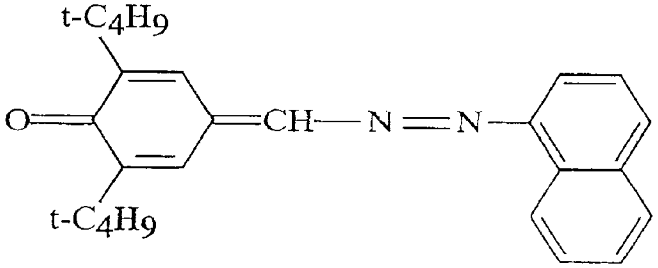
Figure 6B:
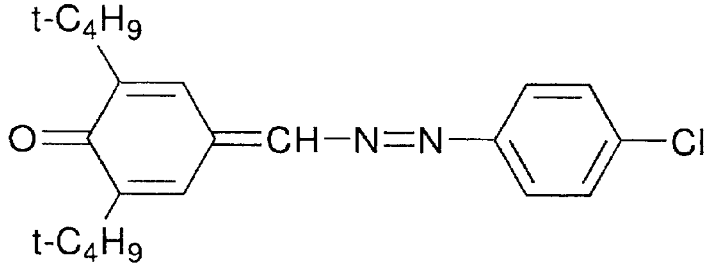
Figure 6B:
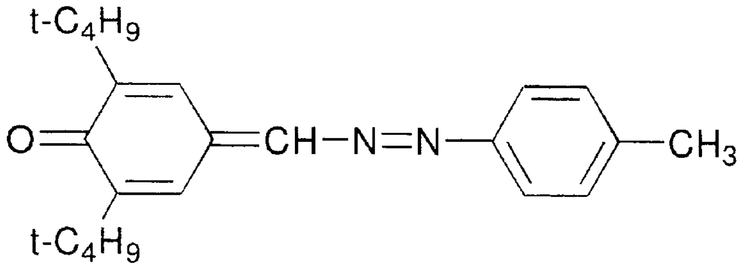

The invention will be explained hereinafter with reference to the accompanying figures and in connection with the preferred embodiments. FIG. 1 is a cross section of a single-layer type electrophotographic photoconductor. FIG. 2 is a cross section of another laminate type electrophotographic photoconductor.

Referring now to FIG. 1, a single-layer-type electrophotographic photoconductor includes an electrically conductive substrate 1 and a photosensitive layer 2 on the conductive substrate 1. The photosensitive layer 2 is a resin binder layer, in which a charge generation agent and a charge transport agent are dispersed. If necessary, a cover layer (protection layer) 6 is laminated on the photosensitive layer 2. The single-layer-type photoconductor is made by dispersing a charge generation agent into a solution, in which a charge transport agent and a resin binder are dissolved, and by coating the dispersion liquid on an electrically conductive substrate 1 to form a photosensitive layer 2. If necessary, a further protection layer 6 coating is formed on the photosensitive layer 2.

Referring now to FIG. 2, a laminate-type electrophotographic photoconductor includes an electrically conductive substrate 1 and a photosensitive layer laminate 5 on the conductive substrate 1. The photosensitive layer laminate 5 includes a charge generation layer 3 and a charge transport layer 4. The charge generation layer contains a charge generating agent as its main component. The charge transport layer 4 contains a charge transport agent and is laminated onto the charge generating layer 3. This type of electrophotographic photoconductor is made by dispersing particles of a charge generating agent into a solvent or a resin binder and depositing the charge generating agent onto a conductive substrate by either vacuum deposition or by coating the substrate with the dispersion liquid followed by drying. A charge transport agent is either dissolved or dispersed into a resin binder, coated onto the charge generating layer and then dried.

The photoconductor of any type according to the invention contains the electron transport compound described by the general formula (I) or (II) as a charge transport agent.

The laminate type photoconductor will be explained in greater detail with reference to FIG. 2. Referring now to FIG. 2, the electrically conductive substrate 1 works as an electrode of the photoconductor and a support of the other layers. The substrate 1 may be shaped as a cylindrical tube, plate or a film. The substrate 1 may be made of a metallic material such as aluminum, stainless steel and nickel or an insulative material such as glass and resin having a treated surface so that it may be electrically conductive.

The charge generation layer 3 is formed by dispersing particles of an electron generation agent into a resin binder and depositing the electron generation agent using the vacuum deposition method. The charge generation layer 3 generates charges in response to the light that the charge generation layer 3 receives. It is important for the charge generation layer 3 to generate charges with a high charge generation efficiency and to inject the generated charges efficiently to the charge transport layer 4 with little electric field dependence and even under a low electric field. Pigments including phthalocyanine compounds such as metal-free phthalocyanine and titanyl phthalocyanine, azo compounds, quinone compounds, indigo compounds, cyanine compounds, squalane compounds, azulenium compounds and pyrylium compounds, coloring materials, selenium and selenium compounds are used for the charge generation agent. An appropriate charge generation agent may be selected considering the wavelength range of the exposure light source used for image formation. It is desirable for the charge generation layer to be as thin as possible but still thick enough to generate sufficient charges. The charge generation layer is usually 5 μm thick or less, and, preferably, 2 μm thick or less. The charge generation layer may contain a charge transport agent and other such ingredients added to the main component, i.e. charge generation agent.

Polycarbonate resins, polyester resins, polyamide resins, polyurethane resins, vinyl chloride resins, phenoxy resins, poly(vinyl butyral) resins, diacryl phthalate resins, methacrylate polymers and copolymers of these resins and polymers are used alone or in an appropriate combination for the resin binder of the charge generation layer.

The charge transport layer 4 is a coating layer containing a resin binder and an electron transport compound, described by the general formula (I) or (II) and dispersed into the resin binder, as a charge transport agent. The charge transport layer 4 works as an insulator for retaining the charges of the photoconductor in the dark and transports the charges injected from the charge generation layer in response to light exposure.

Polymers such as polycarbonate, polyester, polystyrene and methacrylate and copolymers of these polymers are used for the resin binder of the charge transport layer.

An antioxidant such as amine antioxidants, phenol antioxidants, sulfur antioxidants, phosphite antioxidants, phosphorus antioxidants may be added to the charge transport layer 4 to prevent the photoconductor from being deteriorated by ozone.

The cover layer 6 in FIG. 1 receives and retains the charges of the corona discharge in the dark. It is necessary for the cover layer 6 to be transparent enough to the exposure light, so that the photosensitive layer is sensitive, and to transmit the exposure light to the photosensitive layer. It is also necessary for the cover layer 6 to receive the generated charges and to neutralize and eliminate the surface charges. Polyester, polyamide and other such organic insulative materials are used for the cover layer 6. These organic materials may be mixed with glass, $SiO_2$ and other such inorganic materials, or with metal and metal oxide which reduce the electrical resistance. As described above, it is desirable for the material of the cover layer 6 to be transparent as much as necessary in the wavelength range of the optical absorption maximum of the charge generating agent.

Although it depends on the compositions, the thickness of the cover layer is set arbitrarily as long as it does not cause adverse effects such as residual potential rise under repeated use of the photoconductor.

Embodiments

The following examples serve to illustrate the preferred method of synthesizing the compounds of this invention.

Synthesis of the Compound Described by the Structural Formula (I-1)

Step1: Synthesis of the Compound Described by the structural formula (III)

Figure 15:
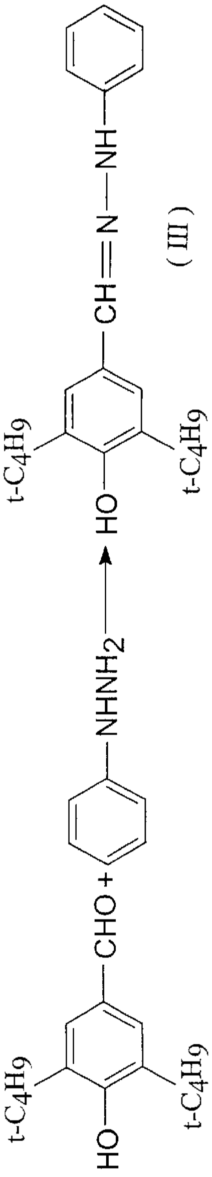
FIG. 15 shows the synthesis flow of the compound described by the structural formula (III).

The compound described by the structural formula (III) was synthesized as shown FIG. 15.

To a stirred solution of 23.67 g of 3,5-di-t-butyl-4-hydroxybenzaldehyde and 10.83 g of phenylhydrazine in 300 mL of ethanol was added 2 drops of 35 HCl. The mixture was refluxed for 2 hr. After cooling to ambient temperature, the raw materials were collected by filtration. The residue was recrystallized from a mixture of methanol and ethanol to give 22.68 g (70%) of the compound described by the structural formula (III).

Step2: Synthesis of the Compound Described by the Structural Formula (I-1)

Figure 16:
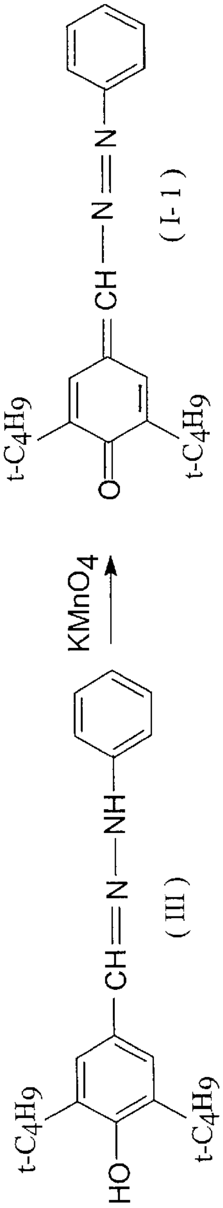
FIG. 16 shows the synthesis flow of the compound described by the structural formula (I-1).

The compound described by the structural formula (I-1) was synthesized as shown FIG. 16.

Figure 27A:
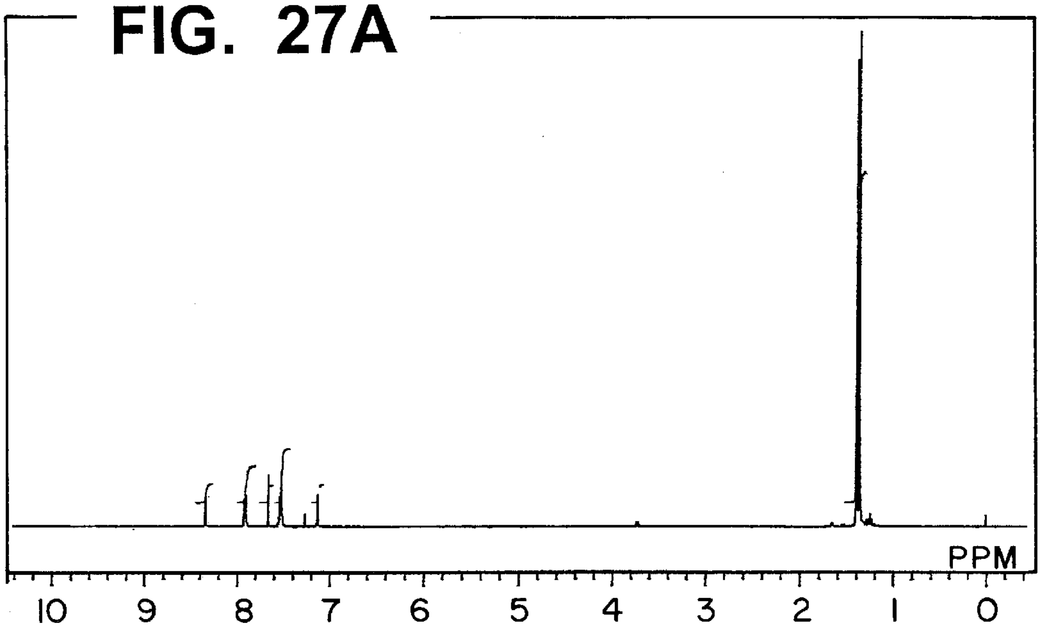
FIGS. 27A and 27B show $^1$H NMR spectrum and $^{13}$C NMR spectrum of the compound described by the structural formula (I-1).
Figure 27B:
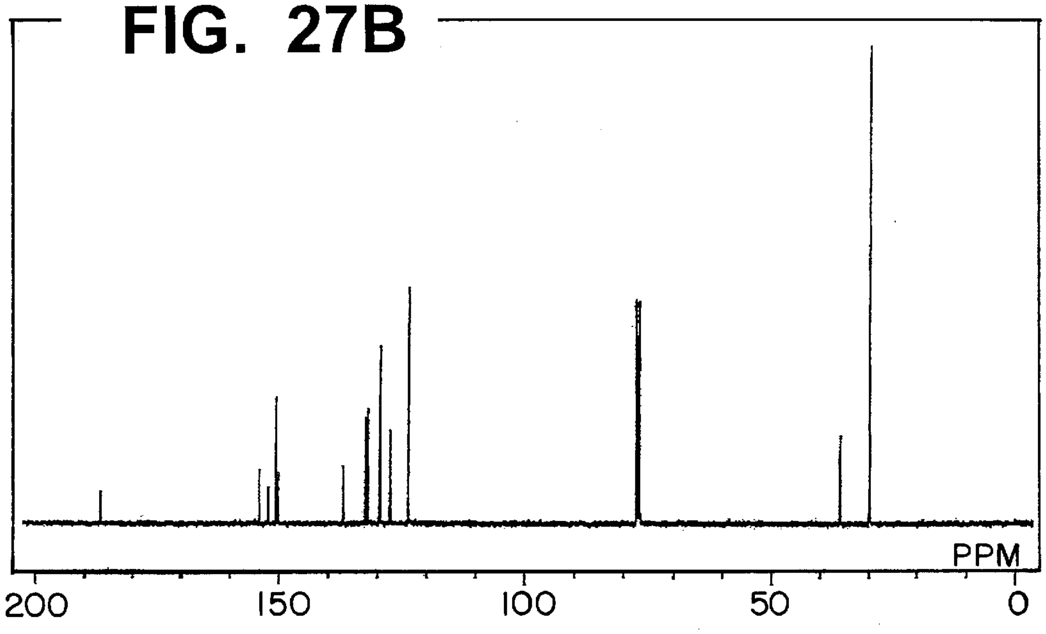

The mixture of 6.62 g of the compound described by the structural formula (III) and 9.99 g of potassium permanganate in 100 mL of chloroform was refluxed for 3 hr. After cooling to ambient temperature, the solution was filtated and evaporated. The crude product was recrystallized from hexane to give 4.00 g (60%) of the compound described by the structural formula (I-1): m.p. 113–114; m/z 322 ($M^+$). NMR spectra of the compound described by the structural formula (I-1) are given in FIGS. 27A and 27B.

Synthesis of the Compound Described by the Structural Formula (I-17)

Step1: Synthesis of the Compound Described by the Structural Formula (III-1)

Figure 17:
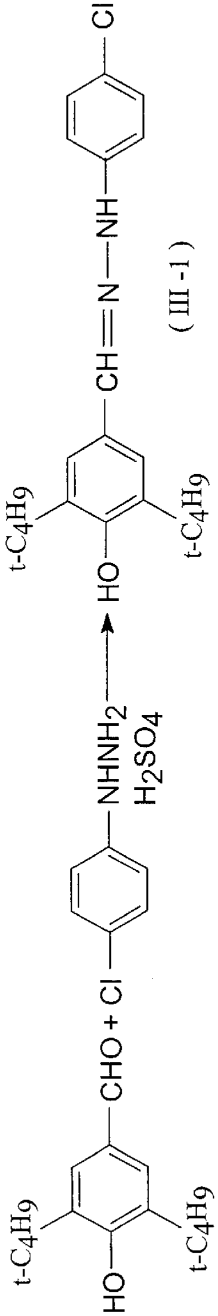
FIG. 17 shows the synthesis flow of the compound described by the structural formula (III-1).

The compound described by the structural formula (III-1) was synthesized as shown FIG. 17.

The mixture of 35.10 g of 3,5-di-t-butyl-4-hydroxybenzaldehyde, 31.60 g of 4-chloro-phenylhydrazine sulfate and 13.55 g of sodium acetate in 300 mL of ethanol was refluxed for 3 hr. After cooling to ambient temperature, the raw materials were collected by filtration. The residue was recrystallized from a mixture of methanol and ethanol to give 40.68 g (76%) of the compound described by the structural formula (III-1).

Step2: Synthesis of the Compound Described by the Structural Formula (I-17)

Figure 18:
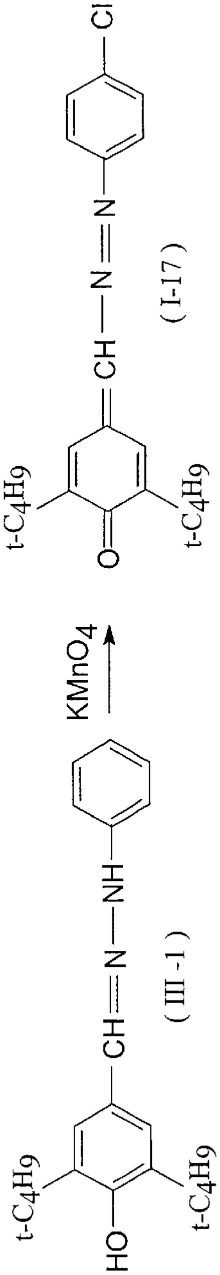
FIG. 18 shows the synthesis flow of the compound described by the structural formula (I-17).

The compound described by the structural formula (I-17) was synthesized as shown FIG. 18.

Figure 28A:
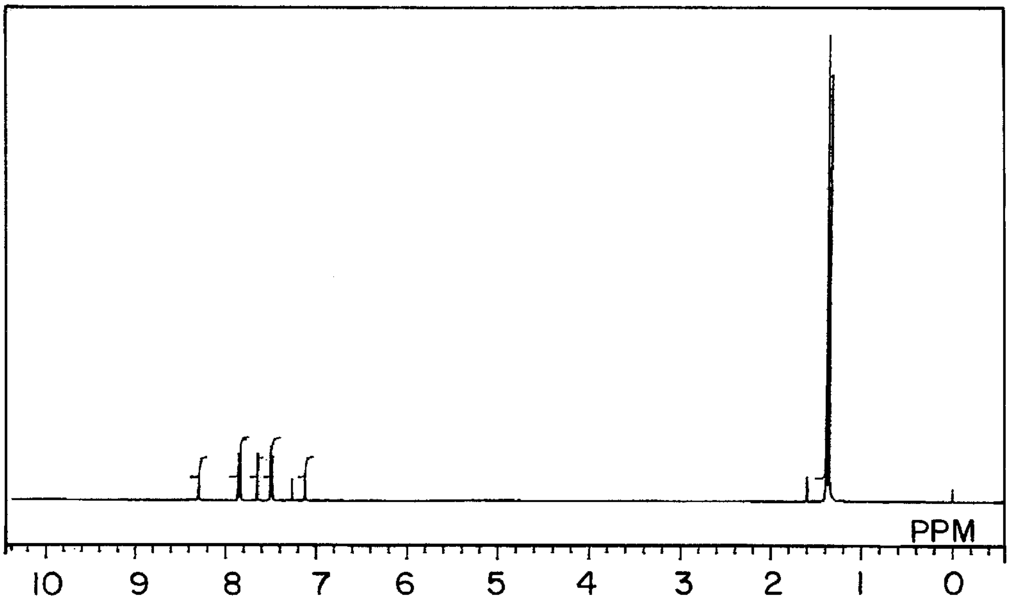
FIGS. 28A and 28B show $^1$H NMR spectrum and $^{13}$C NMR spectrum of the compound described by the structural formula (I-17).
Figure 28B:
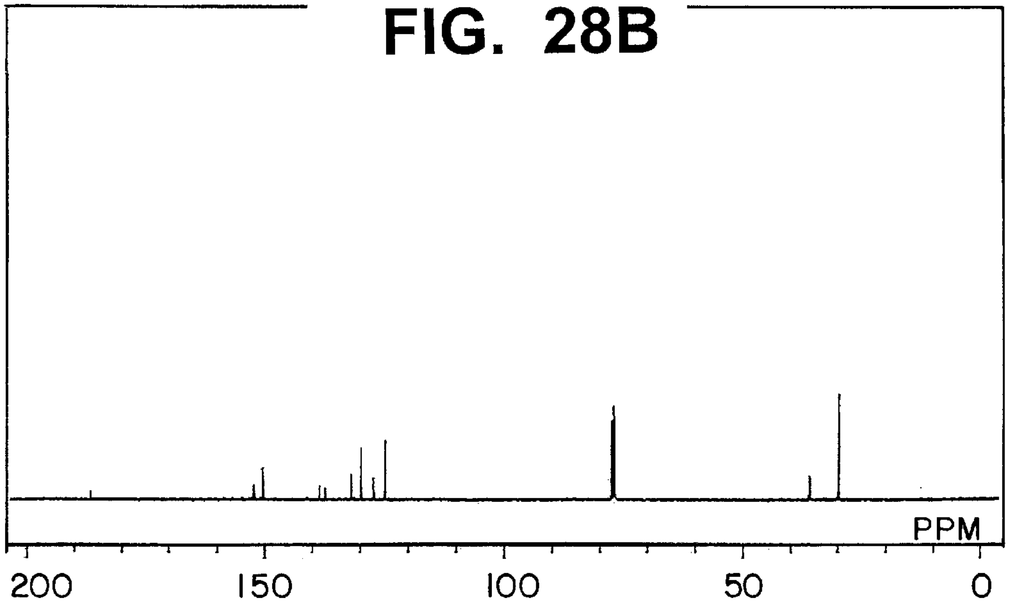

The mixture of 7.23 g of the compound described by the structural formula (I-17) and 4.75 g of potassium permanganate in 50 mL of chloroform was refluxed for 3 hr. After cooling to ambient temperature, the solution was filtated and evaporated. The crude product was recrystallized from hexane to give 5.00 g (69%) of the compound described by the structural formula (1–17): m.p. 147–149; m/z 356 358($M^+$). NMR spectra of the compound described by the structural formula (I-17) are given in FIGS. 28A and 28B.

Synthesis of the compound described by the structural formula (I-11)

Step1: Synthesis of the Compound Described by the Structural Formula (III-2)

Figure 19:
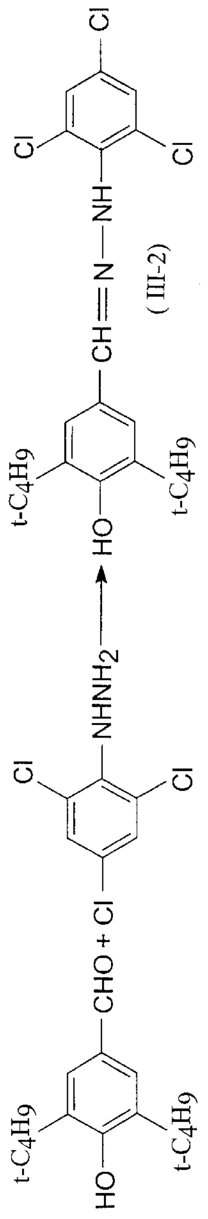
FIG. 19 shows the synthesis flow of the compound described by the structural formula (III-2).

The compound described by the structural formula (III-2) was synthesized as shown FIG. 19.

To a stirred solution of 23.40 g of 3,5-di-t-butyl-4-hydroxybenzaldehyde and 23.30 g of 2,4,6-trichlorophenylhydrazine in 200 mL of ethanol was added 2 drops of 35HCl. The mixture was refluxed for 1 hr. After cooling to ambient temperature, the raw materials were collected by filtration. The residue was recrystallized from ethanol to give 37.01 g (87%) of the compound described by the structural formula (III-2).

Step2: Synthesis of the Compound Described by the Structural Formula (I-11)

Figure 20:
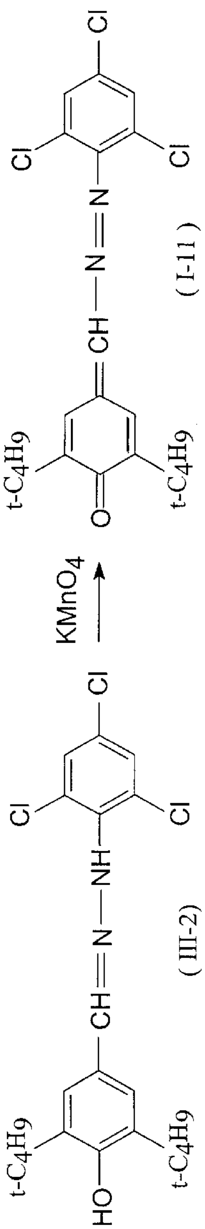
FIG. 20 shows the synthesis flow of the compound described by the structural formula (I-11).

The compound described by the structural formula (I-11) was synthesized as shown FIG. 20.

Figure 29A:
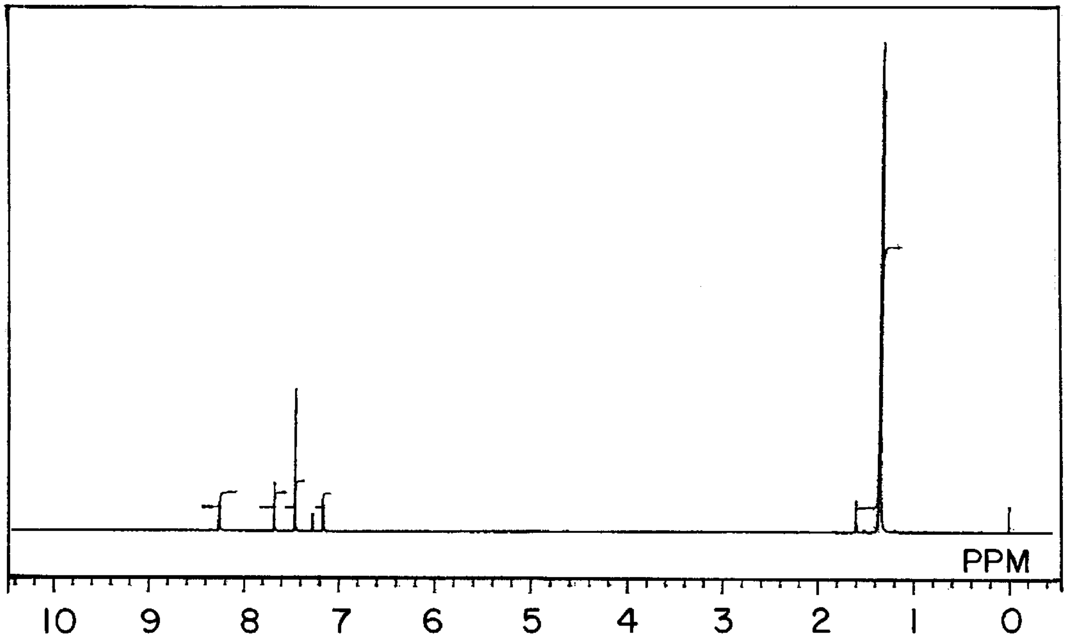
FIGS. 29A and 29B show $^1$H NMR spectrum and $^{13}$C NMR spectrum of the compound described by the structural formula (I-11).
Figure 29B:
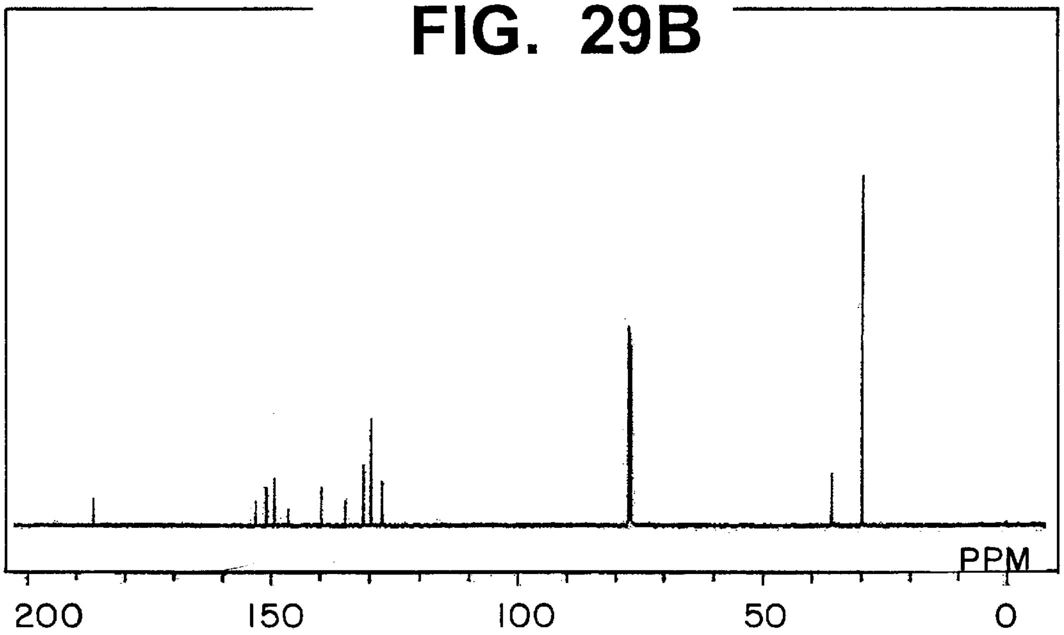

The mixture of 12.80 g of the compound described by the structural formula (111-2) and 7.10 g of potassium permanganate in 75 mL of chloroform was refluxed for 1 hr. After cooling to ambient temperature, the solution was filtated and evaporated. The crude product was recrystallized from a mixture of hexane and toluene to give 6.70 g (53%) of the compound described by the structural formula (I-11): m.p. 116–117; m/z 424 426 428 430($M^+$). NMR spectra of the compound described by the structural formula (I-11) are given in FIGS. 29A and 29B.

Synthesis of the Compound Described by the Structural Formula (I-18)

Step1: Synthesis of the Compound Described by the Structural Formula (III-3)

Figure 21:
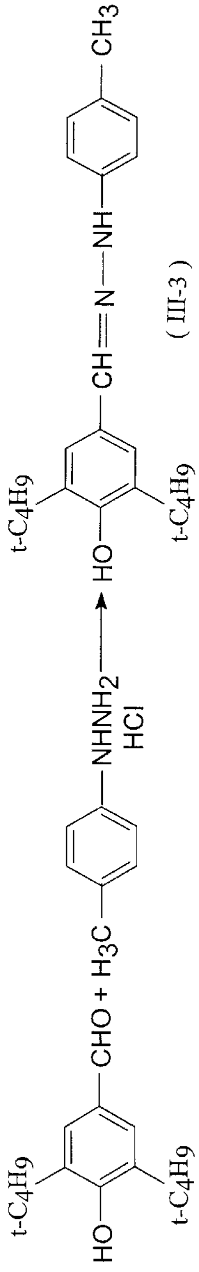
FIG. 21 shows the synthesis flow of the compound described by the structural formula (III-3).

The compound described by the structural formula (III-3) was synthesized as shown FIG. 21.

The mixture of 23.43 g of 3,5-di-t-butyl-4-hydroxybenzaldehyde, 16.71 g of p-tolylhydrazine hydrochloride and 9.02 g of sodium acetate in 200 mL of ethanol was refluxed for 1 hr. After cooling to ambient temperature, the raw materials were collected by filtration. The residue was recrystallized from ethanol to give 20.29 g (60%) of the compound described by the structural formula (I-18).

Step2: Synthesis of the Compound Described by the Structural Formula (I-18).

Figure 22:
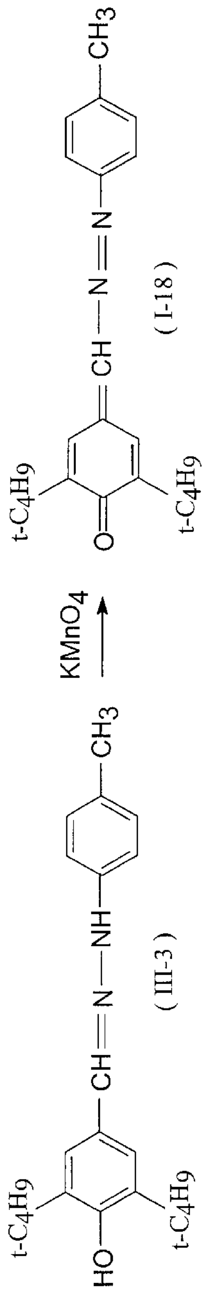
FIG. 22 shows the synthesis flow of the compound described by the structural formula (I-18).

The compound described by the structural formula (I-18) was synthesized as shown FIG. 22.

Figure 30A:
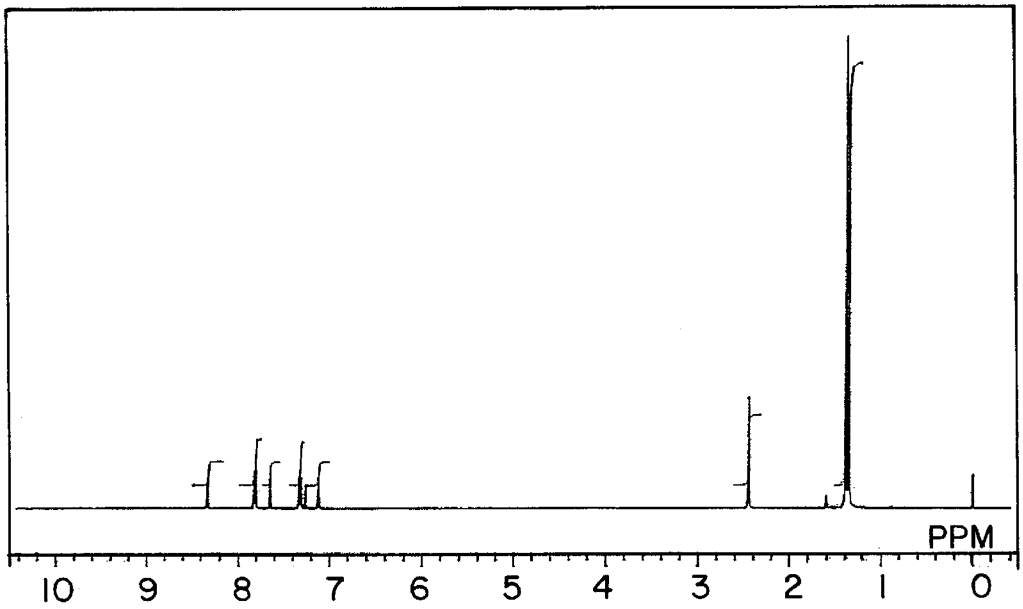
FIGS. 30A and 30B show $^1$H NMR spectrum and $^{13}$C NMR spectrum of the compound described by the structural formula (I-18).
Figure 30B:
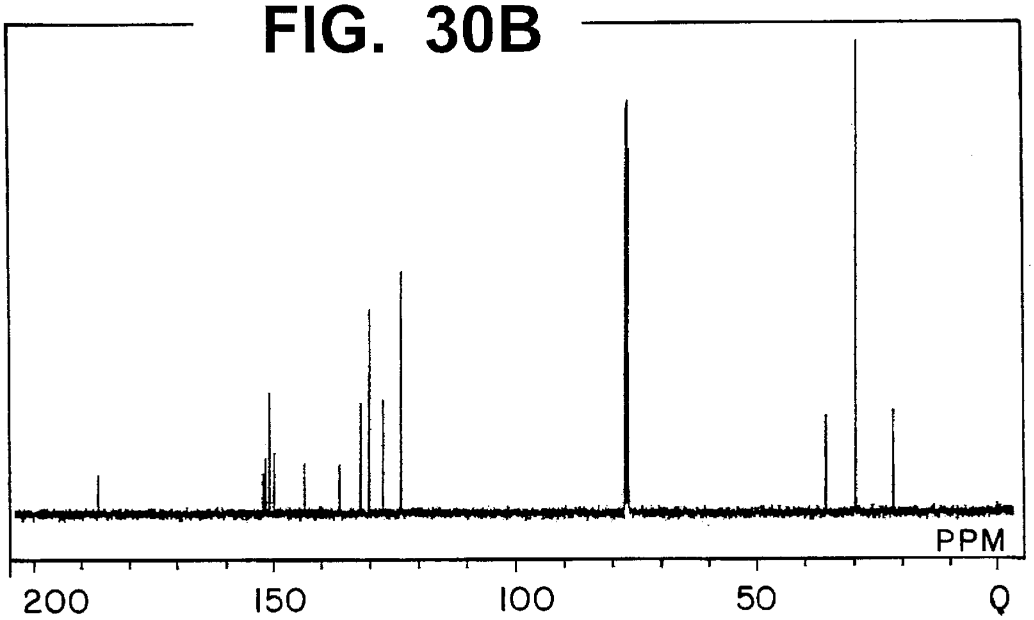

The mixture of 9.89 g of the compound described by the structural formula (III-3) and 7.12 g of potassium permanganate in 80 mL of chloroform was refluxed for 3 hr. After cooling to ambient temperature, the solution was filtated and evaporated. The crude product was recrystallized from hexane to give 4.85 g (49%) of the compound described by the structural formula (I-18): m.p. 122–123 ; m/z 336($M^+$). NMR spectra of the compound described by the structural formula (I-18) are given in FIGS. 30A and 30B.

Synthesis of the Compound Described by the Structural Formula (I-3)

Step1: Synthesis of the Compound Described by the Structural Formula (III-4)

Figure 23:
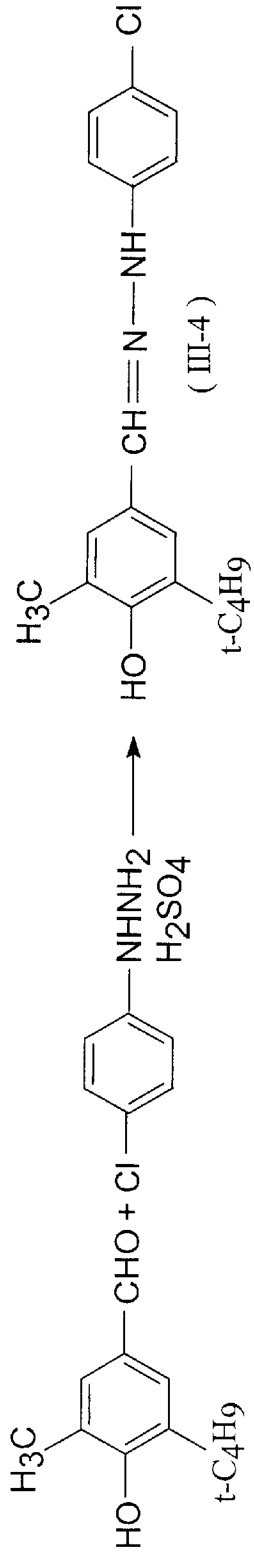
FIG. 23 shows the synthesis flow of the compound described by the structural formula (III-4).

The compound described by the structural formula (III-4) was synthesized as shown FIG. 23.

The mixture of 9.60 g of 3-t-butyl-5-methyl-4-hydroxybenzaldehyde, 9.90 g of 4-chloro-phenylhydrazine sulfate and 4.50 g of sodium acetate in 100 mL of ethanol was refluxed for 1 hr. After cooling to ambient temperature, the raw materials were collected by filtration. The residue was recrystallized from ethanol to give 12.40 g (78%) of the compound described by the structural formula (III-4).

Step2: Synthesis of the Compound Described by the Structural Formula (I-3)

Figure 24:
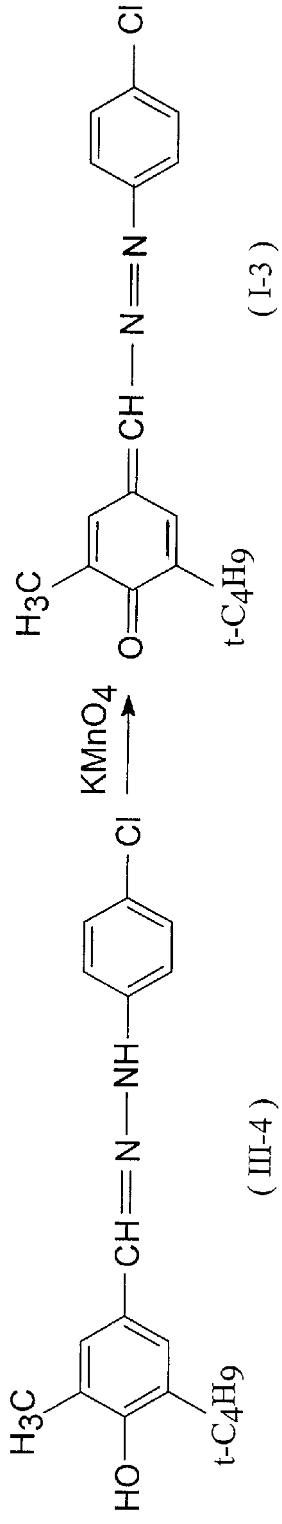
FIG. 24 shows the synthesis flow of the compound described by the structural formula (I-3).

The compound described by the structural formula (I-3) was synthesized as shown FIG. 24.

Figure 31A:
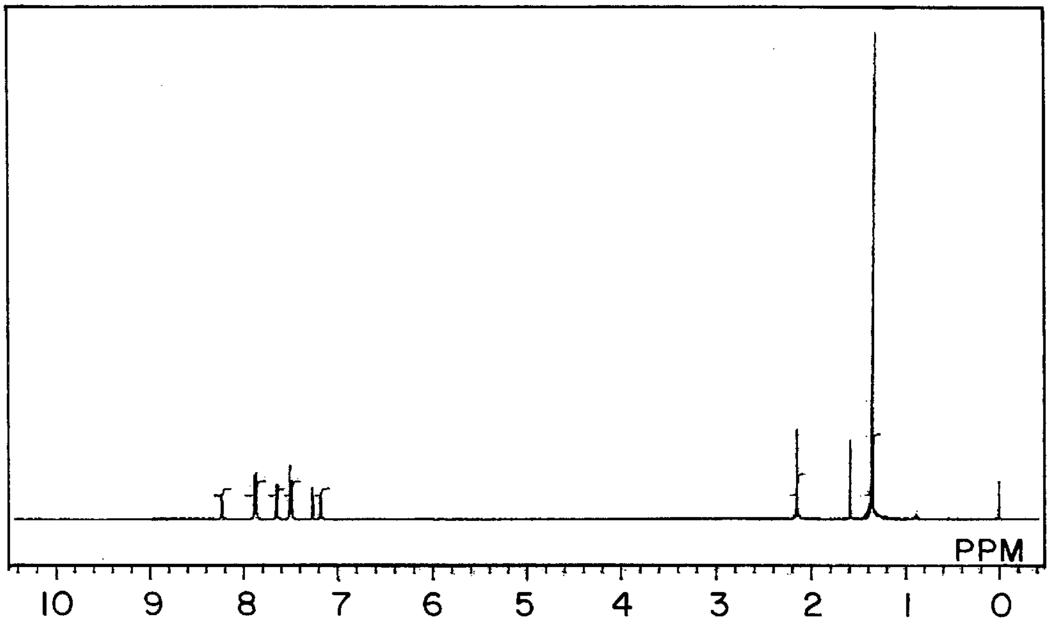
FIGS. 31A and 31B show $^1$H NMR spectrum and $^{13}$C NMR spectrum of the compound described by the structural formula (I3).
Figure 31B:
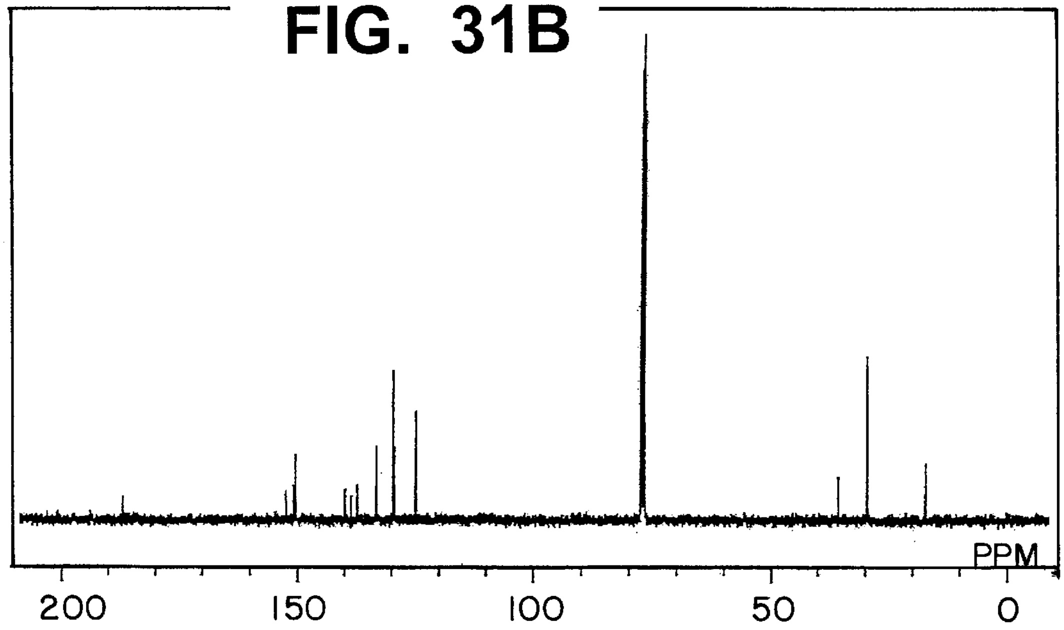

The mixture of 9.50 g of the compound described by the structural formula (III-4) and 9.50 g of potassium permanganate in 100 mL of chloroform was stirred for 3 hr. at room temperature. The solution was filtated and evaporated. The crude product was recrystallized from hexane to give 5.00 g (56%) of the compound described by the structural formula (I-3): m.p. 133–135 m/z 314 316($M^+$). NMR spectra of the compound described by the structural formula (I-3) are given in FIGS. 31A and 31B.

Synthesis of the Compound Described by the Structural Formula (II1)

Step1: Synthesis of the Compound Described by the Structural Formula (IV-1).

Figure 25:
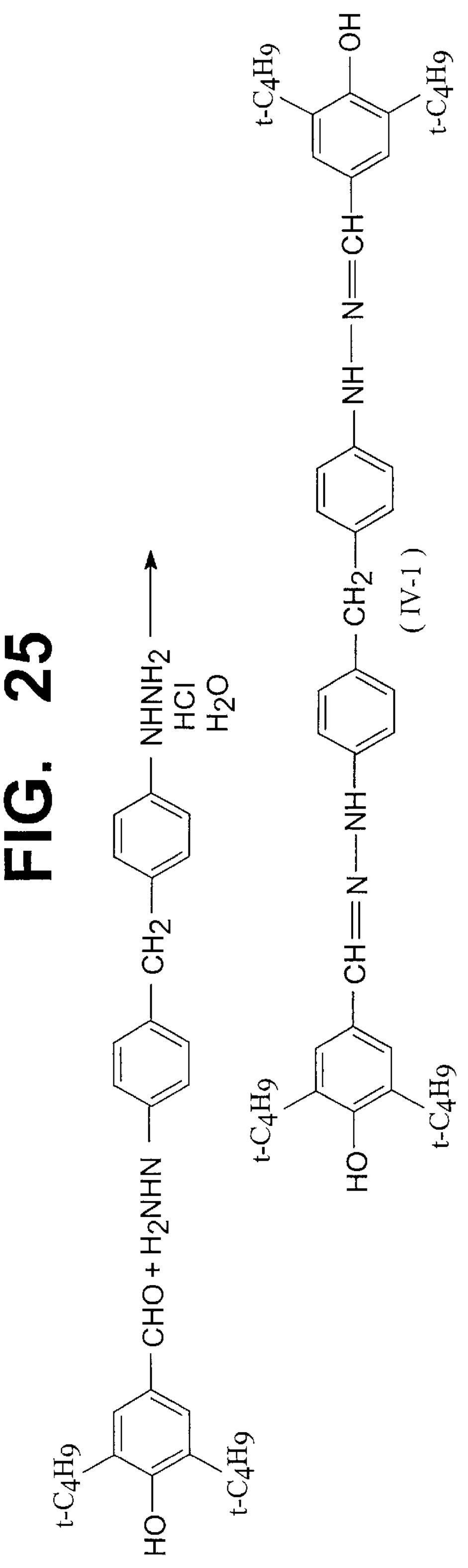
FIG. 25 shows the synthesis flow of the compound described by the structural formula (IV).

The compound described by the structural formula (IV-1) was synthesized as shown FIG. 25.

The mixture of 23.40 g of 3,5-di-t-butyl-4-hydroxybenzaldehyde, 15.60 g of 4,4'-methylene-bis (phenylhydrazine)hydrochloride hydrate and 4.50 g of sodium acetate in 150 mL of ethanol was refluxed for 1 hr. After cooling to ambient temperature, the raw materials were collected by filtration. The residue was recrystallized from ethanol to give 9.10 g (28%) of the compound described by the structural formula (IV-1).

Step2: Synthesis of the Compound Described by the Structural Formula (II-1)

Figure 26:
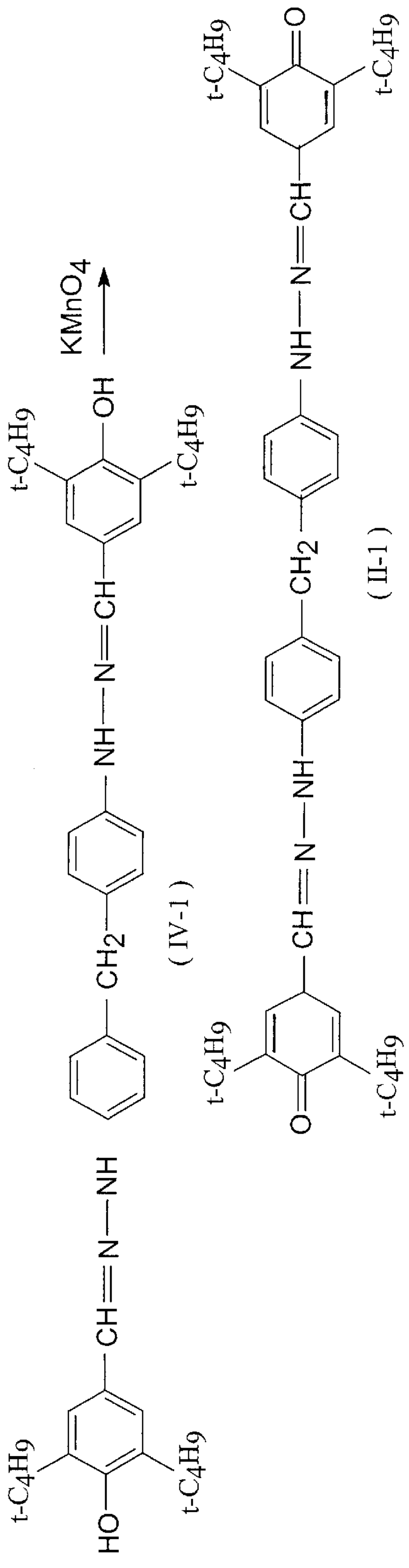
FIG. 26 shows the synthesis flow of the compound described by the structural formula (II-1).

The compound described by the structural formula (II-1) was synthesized as shown FIG. 26.

Figure 32A:
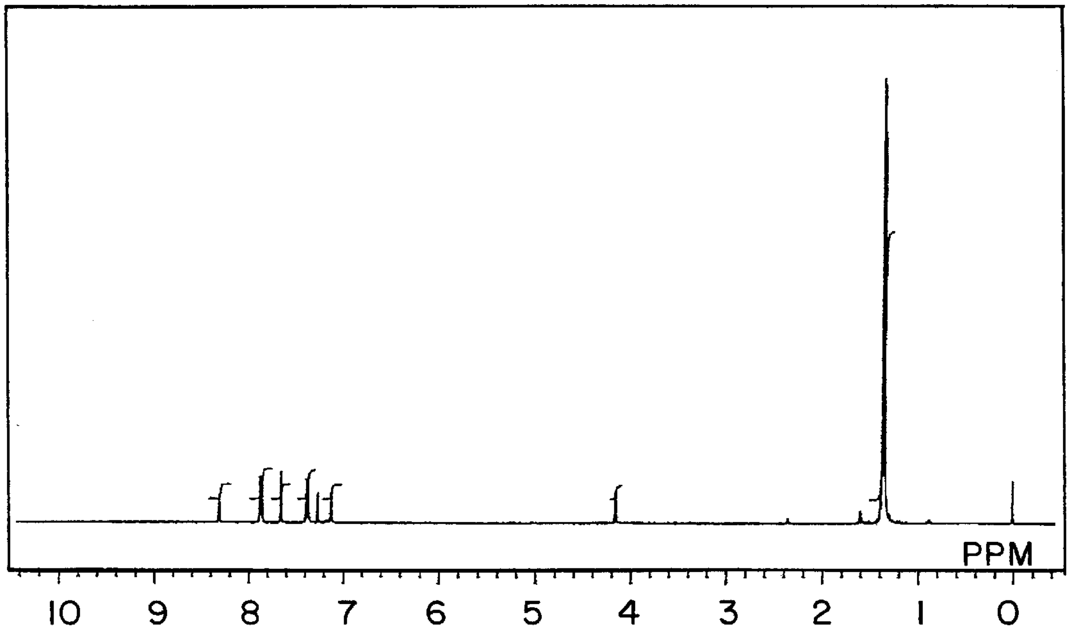
FIGS. 32A and 32B show $^1$H NMR spectrum and $^{13}$C NMR spectrum of the compound described by the structural formula (II-1).
Figure 32B:
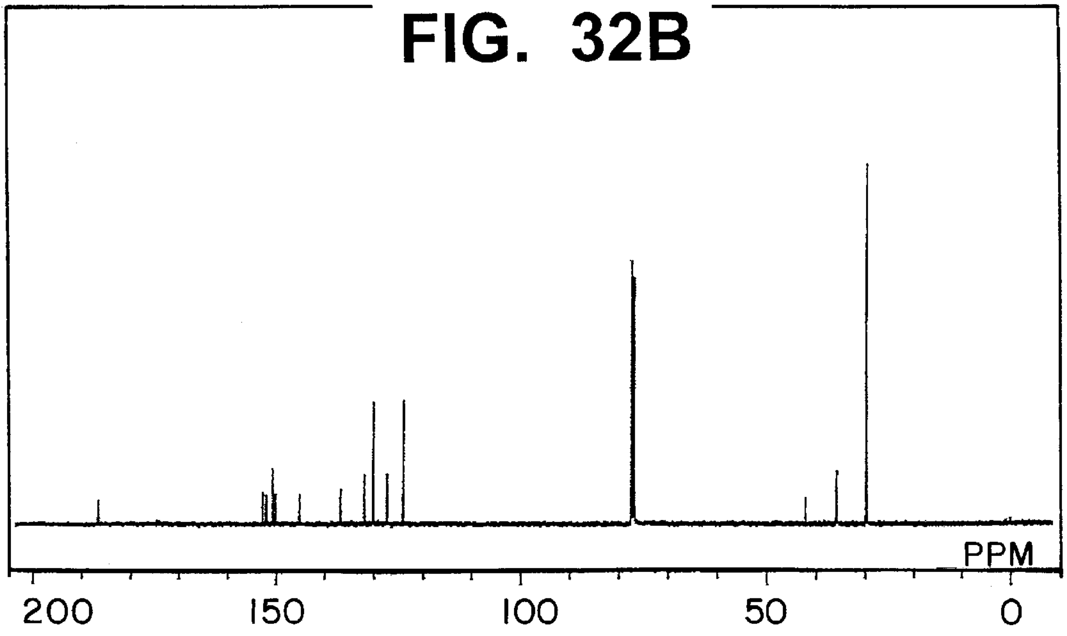

The mixture of 8.60 g of the compound described by the structural formula (IV-1) and 6.20 g of potassium permanganate in 50 mL of chloroform was refluxed for 2 hr. After cooling to ambient temperature, the solution was filtated and evaporated. The crude product was recrystallized from a mixture of hexane and toluene to give 2.80 g (33%) of the compound described by the structural formula (II-1): m.p. 185–186; m/z 656($M^+$). NMR spectra of the compound described by the structural formula (II-1) are given in FIGS. 32A and 32B.

Melting points are uncorrected. NMR spectra were recorded on a JEOL EX-400 spectrometer (400 MHz for $^1H$ and 100 MHz for $^{13}C$) in $CDCl_3$ using tetramethylsilane as the internal standard. Mass spectra were recorded on a Shimadzu Model QP-5050A mass spectrometer.

Now the present invention will be explained below in connection with the preferred embodiments thereof.

First Embodiment (E1)

Coating liquid is prepared by masticating 20 weight parts of X-type metal-free phthalocyanine ($H_2Pc$), 100 weight parts of a compound described by the structural formula (I-1) and 100 weight parts of polyester resin (VYLON 200 supplied from TOYO BO CO., LTD.) with tetrahydrofuran (THF) in a masticator for 3 hr. The coating liquid is coated and dried on an electrically conductive aluminum cylindrical tube (substrate), 30 mm in outer diameter and 260 mm in length, resulting in a photosensitive layer. The resulting photosensitive layer is 12 $\mu$m thick when dry.

Second Embodiment (E2)

Figure 10:
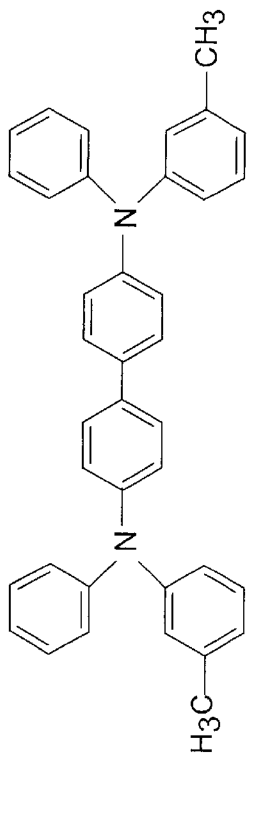
FIG. 10 describes the structural formula of a benzidine derivative used in the photosensitive layer according to the present invention.

Coating liquid is prepared by masticating 2 weight parts of X-type metal-free phthalocyanine ($H_2Pc$), 40 weight parts of a compound described by the structural formula (I-2), 60 weight parts of a benzidine derivative described by the structural formula in FIG. 10 and 100 weight parts of polycarbonate resin (PCZ-200 supplied from MITSUBISHI GAS CHEMICAL COMPANY, INC.) with methylene chloride in a masticator for 3 hr. The coating liquid is coated and dried on an aluminum substrate, resulting in a photosensitive layer. The resulting photosensitive layer is 20 $\mu$m thick when dry.

Third Embodiment (E3)

Coating liquid is prepared by masticating 2 weight parts of titanyl phthalocyanine (TiOPc), 40 weight parts of a compound described by the structural formula (I-3), 60 weight parts of a benzidine derivative described by the structural formula in FIG. 11 and 100 weight parts of polycarbonate resin (BP-PC supplied from IDEMITSU KOSAN CO., LTD.) with methylene chloride in a masticator for 3 hr. The coating liquid is coated and dried on an aluminum substrate, resulting in a photosensitive layer. The resulting photosensitive layer is 20, $\mu$m thick when dry.

Fourth Embodiment (E4)

Coating liquid according to the fourth embodiment is prepared in the same way as the coating liquid of the third embodiment except that a squalane compound described by the structural formula in FIG. 12 is used instead of titanyl phthalocyanine and a compound described by the structural formula (II-1) is used instead of the compound described by the structural formula (I-3).

Fifth Embodiment (E5)

Coating liquid for the charge generation layer is prepared by masticating 70 weight parts of titanyl phthalocyanine (TiOPc) and 30 weight parts of vinyl chloride copolymer (MR-110 supplied from Nippon Zeon Co., Ltd.) with methylene chloride in a masticator for 3 hr. The coating liquid is coated on an aluminum substrate, resulting in a charge generation layer. The resulting charge generation layer is 1 $\mu$m thick. Then, coating liquid for the charge transport layer is prepared by mixing 100 weight parts of a compound described by the structural formula (II-2), 100 weight parts of polycarbonate resin (PCZ-200 supplied from MITSUBISHI GAS CHEMICAL COMPANY, INC.), 0.1 weight parts of silicone oil and methylene chloride. The coating liquid is coated on the charge generation layer, resulting in a charge transport layer. The resulting charge transport layer is 10 $\mu$m thick.

Sixth Embodiment (E6)

A charge generation layer is formed in the same way as that of the fifth embodiment except that a bisazo pigment described by the structural formula in FIG. 13 is used instead of titanyl phthalocyanine. Then, coating liquid for the charge transport layer is prepared by mixing 100 weight parts of a compound described by the structural formula (II-1), 100 weight parts of polycarbonate resin (BP-PC supplied from IDEMITSU KOSAN CO., LTD.), 0.1 weight parts of silicone oil and methylene chloride. The coating liquid is coated on the charge generation layer, resulting in a charge transport layer. The resulting charge transport layer is 10 $\mu$m thick.

Seventh Embodiment (E7)

A charge generation layer is formed in the same way as that of the fifth embodiment except that a bisazo pigment described by the structural formula in FIG. 14 is used instead of titanyl phthalocyanine. Then, coating liquid for the charge generation layer is prepared by mixing 100 weight parts of a compound described by the structural formula (II-2), 100 weight parts of polycarbonate resin (BP-PC supplied from IDEMITSU KOSAN CO., LTD.), 0.1 weight parts of silicone oil and methylene chloride. The coating liquid is coated on the charge generation layer, resulting in a charge transport layer. The resulting charge transport layer is 10 $\mu$m thick.

Evaluation

The electrophotographic properties of the photoconductors fabricated according to the embodiments are evaluated.

The surface potential of the photoconductor is measured as an initial surface potential Vs (V), when the surface is positively electrified by the corona discharge of +4.5 kV in the dark. Then, the surface potential of the photoconductor is measured as a surface potential Vd (V), when the photoconductor is been stored in the dark for 5 sec. after the corona discharge is stopped. Then, the half-decay time (sec.) of the surface potential Vd (V) is measured as the sensitivity $E_{1/2}$ (lux.sec), when the photoconductor surface is irradiated with white light at the illuminance of 100 lux.

The surface potential of the photoconductor is measured as a residual potential Vr (V), when the surface is irradiated with white light at the illuminance of 100 lux for 10 sec. The electrophotographic properties of the photoconductors are also measured at 780 nm wavelength monochromatic light, since it is expected that the photoconductors are more sensitive in the longer wavelength range. The initial potential and surface potential at 780 nm are measured in the same way as described before. The light exposure ($\mu J/cm^2$) at the half decay time is obtained by irradiating the photoconductor surface with 1$\mu$W of 780 nm wavelength monochromatic light in place of the white light. The residual potential Vr (V) is measured after irradiation of the photoconductor surface with monochromatic light for 10 sec. The results are listed in Table 1.

TABLE 1

| | White light | | Monochromatic light (780 mn) | |
|---|---|---|---|---|
| | Sensitivity (lux·s) | Residual potential (V) | Sensitivity ($\mu J/cm^2$) | Residual potential (V) |
| E1 | 6.3 | 110 | 4.3 | 90 |
| E2 | 1.2 | 50 | 0.8 | 30 |
| E3 | 1.1 | 50 | 0.7 | 60 |
| E4 | 1.6 | 60 | 0.8 | 60 |
| E5 | 1.2 | 80 | 1.5 | 60 |
| E6 | 2.3 | 80 | — | — |
| E7 | 2.6 | 90 | — | — |

By using an electron transport compound described by the general formula (I) or (II) for a photosensitive layer on an electrically conductive substrate, a photoconductor is obtained, that exhibits high sensitivity and excellent electrical properties in positive electrification. Furthermore, by selecting an appropriate material from phthalocyanine compounds, squalane compounds, bisazo compounds and other such charge generation agents, considering the kind of the exposure light source, a photoconductor is obtained that may be used in a laser printer, a copying machine and other such electrophotographic apparatuses. If necessary, the durability of the photoconductor may be further improved by disposing a cover layer on the charge transport layer.

2. The electron transport agent according to claim 1, wherein at least one of said $R^1$ substituents is an alkyl group.

3. The electron transport agent according to claim 1, wherein at least one of said $R^2$ substituents is an alkyl group.

4. The electron transport agent according to claim 1, wherein at least one of said $R^1$ substituents is an alkoxy group.

5. The electron transport agent according to claim 1, wherein at least one of said $R^2$ substituents is a substituted or unsubstituted alkoxy group.

6. The electron transport agent according to claim 1, wherein at least one of said $R^1$ substituents is an aryl group.

7. The electron transport agent according to claim 1, wherein at least one of said $R^2$ substituents is an aryl group.

8. The electron transport agent according to claim 1, provided that when m is at least 2 then at least two of said $R^1$ substituents are different from one another.

9. The electron transport agent according to claim 1, provided that when said m is at least two then said $R^1$ substituents are identical.

10. The electron transport agent according to claim 1, provided that when n is at least 2 then at least two of said $R^2$ substituents are different from one another.

11. The electron transport agent according to claim 1, provided that when said n is at least 2 then said $R^2$ substituents are identical.

12. An electron transport compound according to the following formula (II):

(II)

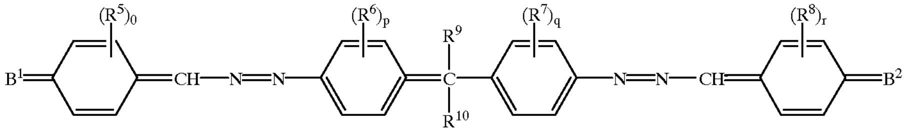

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An electron transport agent according to the following formula (I):

(I)

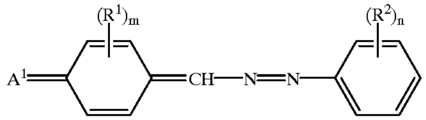

wherein $R^1$ and $R^2$ are each independently selected from the group consisting of a halogen atom, a substituted or unsubstituted alkyl group having from 1 to 8 carbon atoms, a substituted or unsubstituted alkoxy group having from 1 to 8 carbon atoms, an arylalkyl group, a substituted or unsubstituted aryl group, and a residue forming a ring;

$A^1$ is an oxygen atom;

m is an integer from 0 to 4; and n is an integer from 1 to 5.

wherein $R^5$, $R^6$, $R^7$ and $R^8$ are each independently selected from the group consisting of a halogen atom and a substituted or unsubstituted alkyl group having from 1 to 8 carbon atoms;

$R^9$ and $R^{10}$ are each independently selected from the group consisting of a hydrogen atom, an alkyl group having from 1 to 8 carbon atoms and a substituted or unsubstituted aryl group;

$B^1$ and $B^2$ are each an oxygen atom; and o, p, q and r are each independently an integer from 0 to 4.

13. The electron transport compound according to claim 12, wherein at least one of said $R^5$ substituents is an alkyl group.

14. The electron transport compound according to claim 12, wherein at least one of said $R^6$ substiutents is an alkyl group.

15. The electron transport compound according to claim 12, wherein at least one of said $R^7$ substituents is an alkyl group.

16. The electron transport compound according to claim 12, wherein at least one of said $R^8$ substituents is an alkyl group.

17. The electron transport compound according to claim 12, wherein at least one of said $R^9$ substituents is an aryl group.

18. The electron transport compound according to claim 12, wherein at least one of said $R^{10}$ substituents is an aryl group.

19. The electron transport compound according to claim 12, provided that when said o is at least 2 then said $R^5$ substituents are identical.

20. The electron transport compound according to claim 12, provided that when said o is at least 2 then said $R^5$ substituents are different from one another.

21. The electron transport compound according to claim 12, provided that when said p is at least 2 then said $R^6$ substituents are identical.

22. The electrontransport compound according to claim 12, wherein said $R^6$ substituent is an alkyl group.

23. The electron transport compound according to claim 12, provided that when said p is at least 2 then at least two of said $R^6$ substituents are different from one another.

24. The electron transport compound according to claim 12, provided that when said q is at least 2 then said $R^7$ substituents are identical.

25. The electron transport compound according to claim 12, provided that when said q is at least 2 then at least two of said $R^7$ substituents are different from one another.

26. The electron transport compound according to claim 12, provided that when said r is at least 2 then said $R^8$ substituents are identical.

27. The electron transport compound according to claim 12, provided that when said r is at least 2 then at least two of said $R^8$ substituents are different from one another.

* * * * *